United States Patent [19]
Martakos et al.

[11] Patent Number: 5,897,587
[45] Date of Patent: *Apr. 27, 1999

[54] MULTI-STAGE PROSTHESIS

[75] Inventors: Paul Martakos, Pelham, N.H.; Peter Gingras, Bedford, Mass.; Theodore Karwoski, Hudson; Steve A. Herweck, Nashua, both of N.H.

[73] Assignee: Atrium Medical Corporation, Hudson, N.H.

[*] Notice: This patent issued on a continued prosecution application filed under 37 CFR 1.53(d), and is subject to the twenty year patent term provisions of 35 U.S.C. 154(a)(2).

[21] Appl. No.: 08/760,113

[22] Filed: Dec. 3, 1996

[51] Int. Cl.⁶ .................................................. A61F 2/06
[52] U.S. Cl. ................................... 623/1; 623/12
[58] Field of Search .................... 623/1, 11, 12; 606/191, 194, 195, 198

[56] References Cited

U.S. PATENT DOCUMENTS

| | | | |
|---|---|---|---|
| Re. 31,618 | 7/1984 | Mano et al. | 3/1.4 |
| 3,105,492 | 10/1963 | Jeckel | 128/334 |
| 3,479,670 | 11/1969 | Medell | 623/12 |
| 3,993,078 | 11/1976 | Bergentz et al. | 623/1 |
| 4,130,904 | 12/1978 | Whalen | 3/1.4 |
| 4,550,447 | 11/1985 | Seller, Jr. et al. | 623/1 |
| 4,629,458 | 12/1986 | Pinchuk | 623/1 |
| 4,731,073 | 3/1988 | Robinson | 623/1 |
| 5,061,276 | 10/1991 | Tu et al. | 623/1 |
| 5,123,917 | 6/1992 | Lee | 623/1 |
| 5,163,951 | 11/1992 | Pinchuck et al. | 623/1 |
| 5,282,847 | 2/1994 | Trescony et al. | 623/1 |
| 5,282,860 | 2/1994 | Matsuno et al. | 623/12 |
| 5,413,597 | 5/1995 | Krajicek | 623/1 |
| 5,534,287 | 7/1996 | Lukic | 427/178 |
| 5,556,426 | 9/1996 | Popadiuk et al. | 623/1 |
| 5,607,478 | 3/1997 | Lentz et al. | 623/1 |

FOREIGN PATENT DOCUMENTS

| | | | |
|---|---|---|---|
| 0233102 | 8/1987 | European Pat. Off. | 623/12 |
| 2248015 | 5/1975 | France | 623/12 |
| WO 96/28115 | 9/1996 | WIPO . | |

OTHER PUBLICATIONS

Distat Brochure, 3 pages, Gore Technologies Worldwide.

*Primary Examiner*—Michael J. Milano
*Assistant Examiner*—Tram A. Nguyen
*Attorney, Agent, or Firm*—Lahive & Cockfield, LLP

[57] ABSTRACT

A porous tube suitable for use as a vascular graft prosthesis and a method of making it is disclosed. It has a structure of porous polytetrafluoroethylene having a fibrous structure of nodes and fibers connecting the nodes together and an integrated intrawall circumferential support adjacent to areas of variable porosity. This invention provides a polytetrafluoroethylene polymer in a porous form useful as artificial internal organs for, for example vascular bypass, vascular access, and endovascular prosthesis. PTFE walls with radial zones of differing porosity are described.

18 Claims, 2 Drawing Sheets

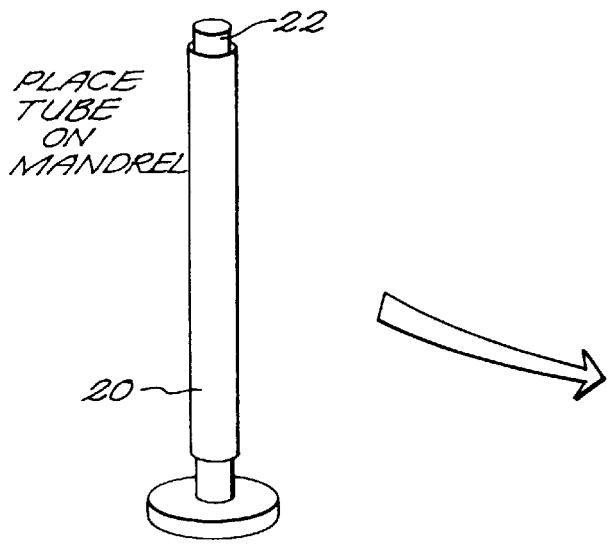
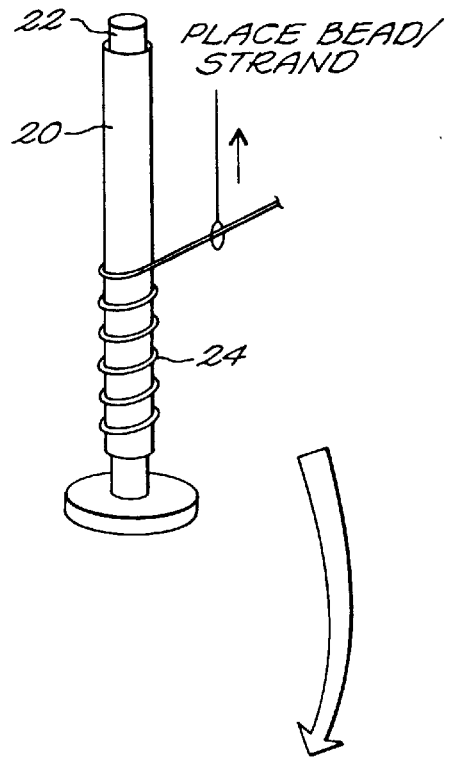
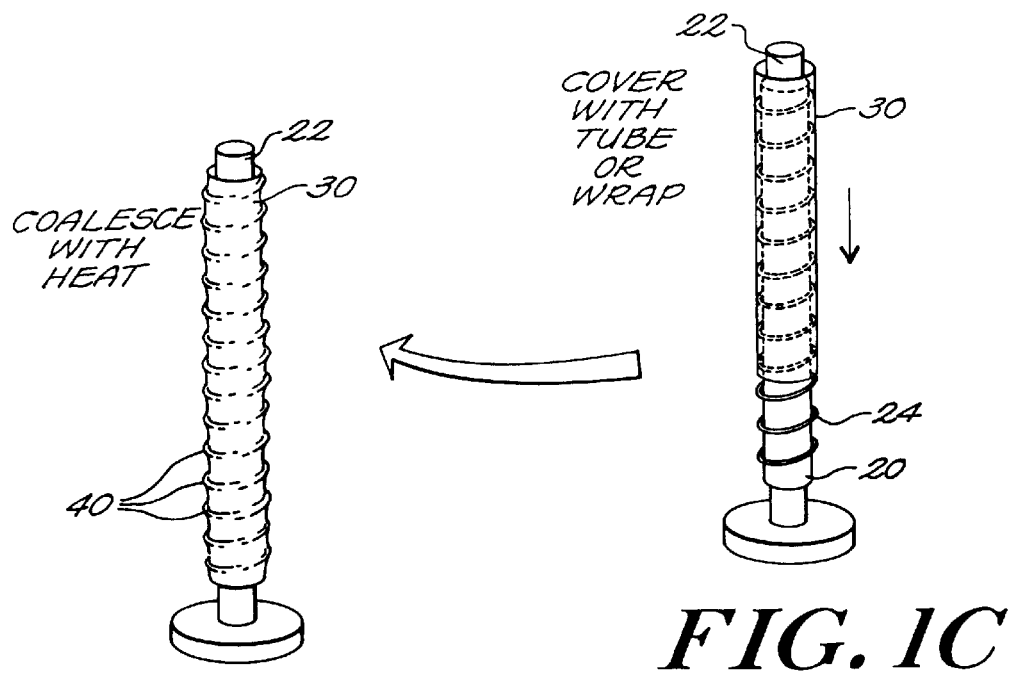

MULTI-STAGE PROSTHESIS

REFERENCE TO RELATED PATENTS AND PATENT APPLICATIONS

This application relates to the commonly owned United States Patent Applications having the following titles and attorney docket numbers, which are being filed by applicant of even date herewith: VASCULAR ENDOPROSTHESIS AND METHOD, U.S. Ser. No. 08/759,861, now pending, PROSTHESIS WITH IN-WALL MODULATION, U.S. Ser. No. 08/760,115, now U.S. Pat. No. 5,824,050; and EXPANDABLE SHIELDED VESSEL SUPPORT, U.S. Ser. No. 08/759,877, now pending. It also relates to applicants' earlier U.S. Pat. Nos. 5,433,909 and U.S. Pat. No. 5,474,824. The foregoing patents describe methods of making extruded PTFE material having large oriented nodes, uniaxially oriented fibrils and a pore structure of oriented channels that differs at different surfaces, or that varies along the thickness dimension of the material. The aforesaid patent applications each describe constructions or methods of use for prostheses, which are further useful in the embodiments and applications of the present invention. Each of the aforementioned United States Patents and Patent Applications is hereby incorporated by reference herein in its entirety.

BACKGROUND OF THE INVENTION

1. Field of the Invention

This invention relates to a porous polytetrafluoroethylene structure that can be formed into an implanted prosthesis with improved physical strength and surgical handling (kink and compression resistance, and ease of tunneling during surgical placement), along with improved mechanical performance (resistance to dilation and physical strength degradation) in arteriovenous applications. It also relates to a method of manufacture of that structure.

2. Description of the Prior Art

Conventional vascular grafts manufactured from porous polytetrafluoroethylene have limitations in surgical handling and healing. In some instances, the porous grafts are wrapped with an external reinforcing film to increase radial strength. Vascular grafts may also be reinforced with an external spiral bead or ring. The reinforcing film does not provide radial support to prevent kinking and collapse during placement or during access use. Furthermore, the presence of an external bead or ring results in interference during surgical placement increasing trauma to the surrounding tissue. In addition, such grafts may be stiff and noncompliant to the natural artery.

Surgical implantation procedures require placement of the vascular graft within the subcutaneous tissue of humans. Peripheral and angioaccess vascular procedures require an anatomic or subcutaneous pathway commonly called tunneling. Tunneling is an initial surgical step in the vascular procedure which can result in localized injury to adjacent tissue. The tunnel diameter relative to the implant diameter, as well as the abrasive force exerted by the implant to the adjacent tissue have a significant impact on the resultant healing response.

It is advantageous in the clinical setting to minimize trauma through ease of tunneling. One approach is to use an expensive surgical tool that often results in larger than required pathways influencing the healing response by creating a fibrous capsule that surrounds a fluid sac that does not incorporate the implant.

One problem which can arise with current PTFE arteriovenous grafts is a lifespan limitation due to physical attrition of the graft caused by poor dialysis access technique identified by repeated needle punctures in concentrated areas resulting in ever enlarging holes or tears in the material comprising the graft wall. Maturation of the surrounding tissue incorporating a vascular access graft, to reduce the adventitial space between tunnel and implant, is a prerequisite to use of the graft for subsequent use in dialysis. The maturation time is necessary to prevent tunnel hematomas which can occur from premature graft puncture. For this reason, it is currently recommended that 1 to 4 weeks pass before initial needle puncture is performed.

SUMMARY OF THE INVENTION

Broadly speaking, the present invention provides for an implantable multistage structure which has integral reinforcement within the device wall having properties that allow for improved surgical handling at implantation, reduced tissue trauma to provide improved healing, and improved performance in an arteriovenous device, together with a method for making the same.

The implantable multistage PTFE porous structure of the invention includes an integral circumferential support within the cross-section with one or more thickness zones within the cross-section having smaller than average pore diameter than the other sections, and in which all the zones have been bonded to the adjacent zones completely throughout the interfaces, free of interlaminar peeling.

The multi-stage structure may be in the shape of any suitable medical implantable device. However, the structure of the invention is particularly advantageous when in the form of an implantable tubular prosthesis, such as a vascular graft.

One embodiment of the present invention includes in vivo implantable structures formed with two or more zones of different node/fibril geometry with an integral intrazone circumferential support. An object of this invention is to provide shaped products manufactured from PTFE that are biologically compatible with surrounding tissue. Another object of the present invention is to provide an in vivo implantable material having improved surgical handling and implant performance.

The biologically compatible material of the present invention has excellent compatibility, strength, and surgical handling because of the arrangement of integral support and node/fibril PTFE fibrous structures. Some current vascular prostheses are designed with an external biaxially oriented reinforcement wrap, spiral bead, or ring, in direct contact with adjacent tissue, to provide additional radial strength to a tubular product, but which results in poor surgical handling during placement and poor compliance. Tubes of the present invention provide improved surgical handling during placement which results in quick maturation and tissue incorporation leading to good healing. In addition, tubes of the present invention provide for greater needle holes per unit area without physical strength compromise in order to address the problem of premature physical failure due to poor cannulation technique.

The products of the present invention have a very broad application in medical devices, such as vascular grafts, endovascular devices, and vascular access devices. In a preferred embodiment, each radial cross-section region of the implant can be distinguished from other regions by having different pore size, pore shape, and porosity in conjunction with an intrawall circumferential support integral to the structure. Indeed, the fibril-nodal microstructure throughout the matrix may have the internodal distance, i.e.

pore size, in one section at least two to twenty times that for its adjacent sections. One in vivo material has two cross-section regions. The first region, for example, has an internodal distance of the pores of the PTFE luminal surface of about 20 or 30 microns and a specific node/fibril geometry. In the next zone the internodal distance of the pores is a range from about 1 to about 10 microns and a specific node/fibril geometry, preferably 1 to 5 microns. This pore size is excellent for cell growth mediator permeability, instead of undesired encapsulation. Another embodiment of the present invention includes the luminal surface and second and third zones of material previously described whereby the third zone has a pore size range of 50 to 500 microns and a specific node/fibril geometry, preferably about 50 to 100 microns which is excellent for fibroblast tissue ingrowth, as the healing process progresses. In a further embodiment, a circumferential support having a radius of diameter from 25 to 1000 microns is present within the wall structure to provide kink and compression resistance along with dialysis technique improvement.

As discussed above, one embodiment of the present invention includes an in-vivo implantable material comprising the luminal, second, and third regions in combination with an integral circumferential support previously described. Another embodiment of the present invention includes the luminal, second and third region of material previously described with the third region or the integral support providing a source location for drug delivery.

In a still further preferred embodiment of this invention, a fluoropolymer bead is wrapped around the outer surface of the composite structure under tension. This embodiment is particularly useful in the preparation of vascular grafts. That is, the multistage structure is a tubular shaped structure with maximum compression resistance having particular utility in applications where such properties are extremely advantageous, (i.e., peripheral bypass surgery, endoluminal).

The above described devices do not have to be totally implanted within the body to be considered within the scope of the present invention and include, among other devices, catheters, transcutaneous tubing or artificial skin.

DESCRIPTION OF THE DRAWING

In the drawing:

FIG. 1A through 1D is a schematic illustration of a process for manufacturing a tubular prosthesis in accordance with the principles of this invention.

DETAILED DESCRIPTION

Figure 2A:
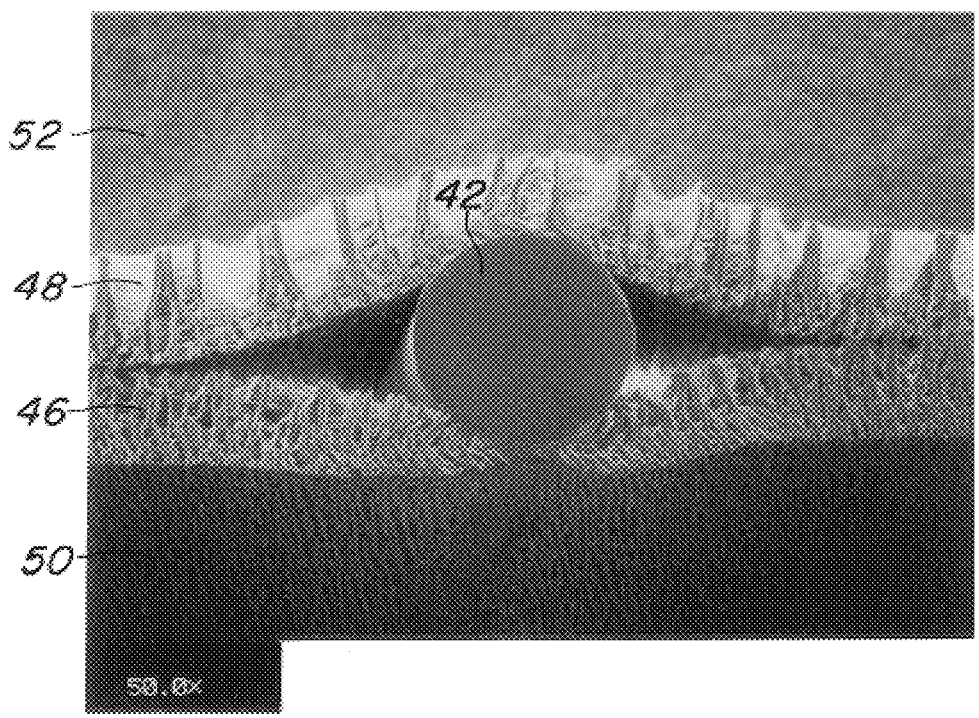
FIGS. 2A and 2B are microphotographs of the wall cross section of two embodiments of an implantable prosthesis constructed in accordance with the principles of this invention.

Expansion of extruded PTFE material is generally known in the art. The structure obtained is a direct result of extrusion and expansion conditions. For example, extrusion variables such as resin type, lubricant levels within the preform, and reduction ratio will have a significant effect on post extrusion processed material. Expansion conditions play a role whereby, in general, material expanded at lower temperatures and faster rates will possess a finer node/fibril structure with higher water entry pressure (WEP) and longitudinal tensile strength (LTS); compared to material expanded at higher temperatures and lower rates which has a coarser node/fibril structure possessing lower WEP, higher radial strength (RBT, RTS), and increased suture strength (SRT).

A PTFE porous tube which can be used in the present invention may be initially produced by a method which is basically the same as the one described in U.S. Pat. No. 5,433,909 and U.S. Pat. No. 5,474,824. The method comprises the step in which a mixture of unsintered PTFE powder and a liquid lubricant is supplied into a ram extruder to extrude in a tubular form, the tube thus obtained is then stretched in the longitudinal direction, while the liquid lubricant is or is not removed from the tube; thereafter while the stretched tube is fixed to prevent shrinkage, the stretched tube is sintered by heating to a sintering temperature of 327° C. or more to fix the stretched structure.

The resulting PTFE porous tube provided has a microfibrous structure comprising nodes interconnected with fibrils. The diameter and length of the fibrils and the size and number of the nodes can be varied by changing the conditions of stretching operations, and thus the pore size and porosity of the porous tube thus obtained can be freely controlled.

As illustrated in the drawing, the structure contemplated by the present invention may be attained by the following procedures. Various porosities of PTFE in a tubular form having a predetermined inner diameter are radially expanded to a size larger than the original diameter, placed on a stainless steel forming mandrel, circumferentially supported with an integral support, and formed to the final configuration, by heating to a temperature of 327° C. or higher until it acquires a multi-stage structure. By this process, the integral support is located between both surfaces of the tube and within the fibrous structure of PTFE. The present invention offers this PTFE porous tube as a tubular prosthesis.

As described above, by appropriately controlling the temperature and time conditions to be employed for stretching operations, along with the arrangement of zones within the wall cross-section, the PTFE tube can be provided with a profile of gradual change in its fibrous structure through the thickness of the tube wall wherein the porous structure of the inner surface is separated from the outside surface.

In a porous, fibrous material, that part of the total porosity which is available to fluid flow is called the "effective porosity". The pressure required to force a liquid into a pore is a function of pore size and geometry, liquid surface tension, and solid/liquid contact angle. Surface tension opposes the entry of any nonwetting liquid (any liquid having a contact angle with surface of the material greater than 90°) into a pore and this opposition may be overcome by external pressure.

In material science, there is a distinction between material porosity and permeability. Porosity is a direct measure of the physical void volume contained within a boundary, whereas permeability refers to the accessibility of that void volume. Permeability is usually expressed as a rate of flow of liquid or gas per unit area, as a function of differential pressure.

Permeability to fluid flow can be determined by measuring the amount of pressure required for water to permeate the pores of the material. To compute water entry pressure (WEP) one subjects the material to an incrementally increasing water pressure until small beads of water appear on the surface. WEP is a gage which can be used to equate porosity to permeability.

Vascular graft porosity is a measure of the void fraction within the prosthesis wall and is believed to give a rough prediction of the capacity of the graft to anchor newly formed surrounding tissue after implantation, whereas permeability is associated with fluid flow through the graft wall.

Vascular permeability or hydraulic conductivity is related to material porosity. Water entry pressure (WEP) is a good measuring technique in this application because it closely mimics the permeation process at the blood/prosthesis interface. WEP is defined as the pressure value necessary to push water into the pores of a synthetic tubular substrate and can be classified as: High (>400 mm Hg), Medium (200–400 mm Hg), and Low (<200 mm Hg).

It has been widely accepted since the nineteenth century that the hydrostatic pressure difference across the arterial wall is capable of transporting water from the blood into the surrounding interstitial space. The filtration coefficients of the wall are dependent on the hydraulic conductivity of both the intima and media. The artery wall is a heterogeneous porous medium in which interstitial fluid can flow through the interstices between cells and tissue mimicking a semi-permeable membrane with hydrostatic and osmotic pressure components. The osmotic pressure difference across the vessel wall is assumed to be small compared with the hydrostatic pressure or hydraulic conductivity.

Expanded PTFE material is characterized by lengthwise-oriented fibrils interrupted by transverse nodes. The pore size in microns is typically determined by measuring fiber length between the nodes (intemodal distance). To compute fibril length, the material is viewed under sufficient magnification. A fibril length is measured from one edge of one node to the edge of an adjacent node. Fibril lengths are measured from the sample to compute a statistically significant mean fibril length.

Nodes and fibrils may be further characterized by their relative geometry. That is, nodes by length, width, and height; and fibrils, by diameter and length. It is the relative geometry of nodes to fibrils, as well as, intemodal distance that determines porosity and permeability of porous PTFE.

As illustrated in FIG. 1A through 1C, the process may be considered in four discrete steps. In step one (FIG. 1A), a tube 20 formed of PTFE resin is placed on a tight-fitting stainless steel forming mandrel 22. The tube 20 may be formed from PTFE resin (Fluon CD-123 obtained from ICI Americas) which has been blended with 100 grams of "Isopar H" odorless solvent (produced by Exxon Corporation) per pound of PTFE, compressed into a preform billet and extruded into a 6.0 mm I.D. and 6.8 mm O.D. tube in a ram extruder having a reduction ratio of about 200:1 in cross-sectional area from billet to extruded tube. After removal of lubricant, the extruded tube is expanded and sintered, according to the method described in the aforesaid U.S. Patents incorporated herein for reference, under various conditions to produce material with different node/fibril structures.

In the next step (FIG. 1B), a bead of diameter less than 1 mm., for example, a 375 micron diameter PTFE bead 24 may be wrapped circumferentially in a helical manner around the tube 20. In a third step (FIG. 1C) a PTFE outer tube or wrap 30 covers the tube 20 with its helically wrapped beads. This tube 30 may be formed using PTFE resin ( FLUON CD-123 obtained from ICI Americas) blended with 100 grams of "Isopar H" odorless solvent (produced by Exxon Corporation) per pound of PTFE, compressed into a preform billet and extruded into a 2.0 mm I.D. and 2.4 mm O.D. tube in a ram extruder having a reduction ratio of about 200:1 in cross-sectional area from billet to extruded tube. After removal of lubricant, the extruded tube was expanded and sintered, according to the method described in the aforesaid US Patents incorporated herein for reference, under various conditions to produce material with different node/fibril structures. This tube 30 is dilated to an 8 mm O.D. prior to placing it over the beaded tube 20.

In the final step (FIG. 1D), the outer tube 30 is restrained to prevent longitudinal shrinkage and is then transferred to an oven at 360° C. for 5 minutes to coalesce the inner and outer tubes 20 and 30 respectively, thereby enclosing and smoothly covering ridges 40, to provide the final structure.

The helical bead 24 is wrapped around tube 20 with a pitch such that the spaced apart protruding ridges 40 are spaced at a distance, such as to 1–3 mm, which is effective to trap a needle inserted into said space thereby preventing longitudinal tearing of the prosthesis when cannulized with a dialysis needle. Preferably the helical winding is wound with a pitch effective to direct the needle to a puncture site at an angle which prevents substantial plowing, hole enlarging and shape deformation.

In an alternative method the first tube 20 is formed of PTFE resin (Fluon CD-123 obtained from ICI Americas) blended with 100 grams of "Isopar H" odorless solvent (produced by Exxon Corporation) per pound of PTFE, compressed into a preform billet, extruded into a 4.0 mm I.D. and 4.6 mm O.D. tube in a ram extruder and having a reduction ratio of about 200:1 in cross-sectional area from billet to extruded tube. After removal of lubricant, the extruded tube is expanded and sintered, according to the method described in the aforesaid US Patents incorporated herein for reference, under various conditions to produce material with different node/fibril structures. The PTFE bead 24 is extruded to a 250 micron diameter, and is circumferentially wrapped in a helical manner. Thereafter an outer tube 30 formed as in the first process is dilated to a 6 mm O.D. and then, as in the prior process embodiment, is heated to coalesce the tubes to form a multistage structure.

In a third process variation the beading 24 may be formed as a metal wire core enveloped by a PTFE jacket.

In a fourth alternate process, rather than a helical winding, discrete bead rings at an axial spacing between one and five millimeters form a segmented supporting structure.

A prosthesis is constructed by the above described methods can include a first tube 20 having a thickness under 0.2 mm, and an outer tube 30 having a membrane thickness under 2.0 mm, the prosthesis preferably having a diameter between 0.5 and 40.0 mm. Preferably, the membrane thickness of the outer tube 30 is less than 1.0 mm.

Figure 2B:
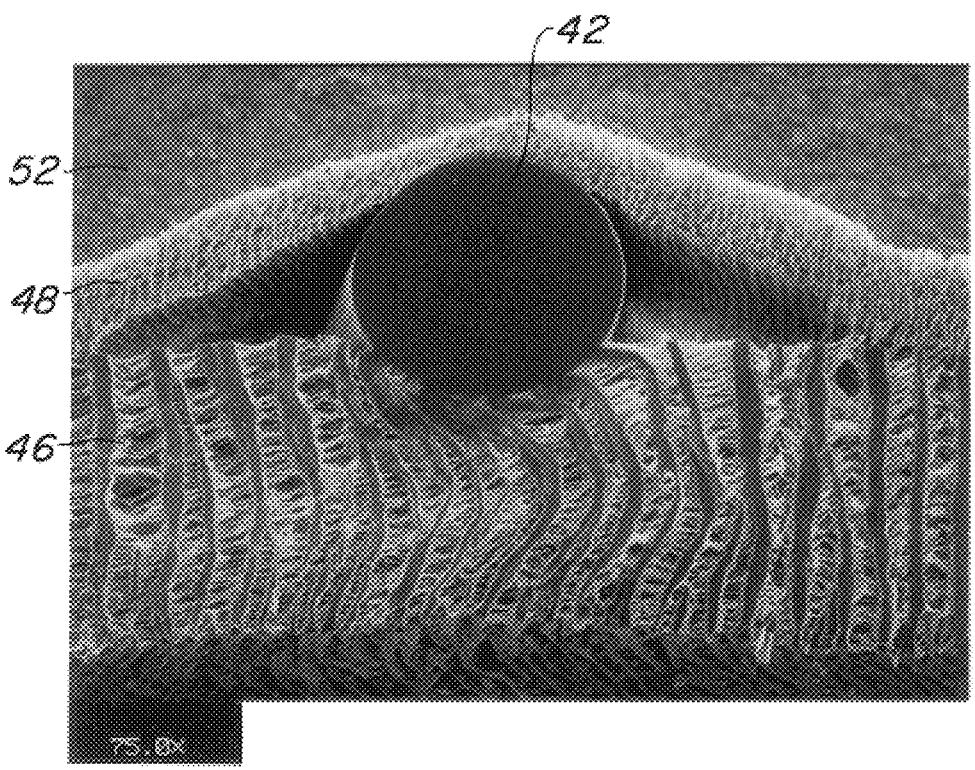

With reference now to FIGS. 2A and 2B, microphotographs at a magnification of 50× of the cross section of a prosthesis wall of two embodiments of a product produced by the above described method are shown. With reference to FIG. 2A, the inner, or luminal, surface 46 of a prosthesis wall is formed of a PTFE material characterized by a relatively low density, and a porosity having relatively large pores interconnected by fibrils. Wrapped around that surface is a bead 42 which as above described can be formed either of a solid PTFE, or by a wire or metal core covered by PTFE. The next zone of the wall is a wrap cover 48 of PTFE which has been coalesced by heat to envelope both the inner surface 46 and the bead 42. In some embodiments the porosity of the cover 48 may be (as illustrated in FIG. 2A) a different porosity than that of the inner surface 46. Finally the outer surface of the prosthesis wall 52 may again be formed of a relatively low porosity PTFE material.

FIG. 2B shows a similar structure at a magnification of 75×, and wherein the porosity of the inner, luminal zone 46 is greater than that of the wrap cover 48.

As indicated in the above examples, the densities and porosities of the PTFE zones maybe varied to meet the specific needs of a particular prosthesis. The invention described herein should be considered as limited by the attached claims, and various embodiments falling within the scope of those claims are intended to be included as part of the present invention.

We claim:

1. An improved tubular prosthesis for surgical implantation to replace a segment of a blood vessel, such prosthesis comprising a first member constituting a flow passage extending along a tube axis and formed of porous polymer, said first member having a first porosity;

at least one support bead disposed on an exterior surface of said first member and extending circumferentially at a regular pitch to form spaced apart transverse ridges having a profile protruding above said exterior surface of said first member; and a polymer membrane placed over said support bead and coalesced to said tube said polymer membrane adhering over the ridges and bonding to said first member to enclose said ridges and provide kink and compression resistance without interlaminar peeling, said membrane further modulating said profile to a smooth undulation for atraumatic tunneling and enhanced surgical handling to reduce abrading of surrounding tissue and said membrane having a second porosity that is substantially less than the first member to prevent needle punctures from causing premature physical failure of the membrane.

2. A tubular prosthesis according to claim 1, wherein said support bead includes a metal wire.

3. A tubular prosthesis according to claim 1, wherein said support bead is wound with a pitch effective to trap a needle from sliding axially and thereby to prevent tearing along the axis of the tube when the prosthesis is subject to cannulization.

4. A tubular prosthesis according to claim 1, wherein said support bead is a bead of solid, non-porous and unexpanded PTFE.

5. A tubular prosthesis according to claim 1, wherein said first tubular member, said support bead and said membrane are coalesced by heat without additional solvent to substantially unitize the prosthesis against delamination.

6. A tubular prosthesis according to claim 1, wherein said prosthesis has a diameter between one half and forty millimeters.

7. A tubular prosthesis according to claim 6, wherein said polymer membrane has thickness under 1.0 millimeters.

8. A tubular prosthesis according to claim 6, wherein said polymer membrane has thickness under two millimeters.

9. A tubular prosthesis according to claim 6, wherein said first tubular member has a thickness under 0.2 millimeters.

10. A prosthesis in accordance with claim 1, wherein said porous polymer and said polymer membrane are each fluoropolymer materials.

11. A tubular prosthesis according to claim 1, wherein said support bead is a polymer coated metal wire.

12. A tubular prosthesis according to claim 10, wherein said support bead has a diameter between 0.025 and 1.0 millimeter.

13. A tubular prosthesis in accordance with claim 1, wherein said support element is wound with a pitch effective to direct a needle to a puncture site at an angle which prevents substantial plowing, hole enlarging and shape deformation.

14. A tubular prosthesis according to claim 1, wherein said support bead is under tension.

15. A tubular prosthesis for surgical implantation to replace a segment of a blood vessel, such prosthesis comprising a first tubular member constituting a flow passage extending along a tube axis and formed of porous polymer, said first tubular member having a first porosity;

at least one body of fluoropolymer extending circumferentially about and forming spaced apart transverse ridges disposed on and protruding above an exterior surface of said first tubular member; and a polymer membrane placed over said body and coalesced to said tubular member to provide a continuous undulant cover adhering over the ridges to modulate the external profile of the assembled prosthesis for atraumatic tunneling, and said ridges being dimensioned and positioned with a pitch effective to direct a dialysis needle to a puncture site without substantial ploughing, hole enlargement and shape deformation, whereby the tubular prosthesis heals to surrounding tissue and provides improved dialysis needle access while avoiding tunnel hematomas and said membrane having a second porosity that is substantially less than the first tubular member to prevent needle punctures from causing premature physical failure of the membrane.

16. A tubular prosthesis according to claim 15, wherein said fluoropolymer material has an elastic limit of deformation greater than that of said polymer.

17. A tubular prosthesis for surgical implantation to replace a segment of a blood vessel, such prosthesis comprising a first tubular member constituting a flow passage extending along a tube axis and formed of porous polytetrafluoroethylene (PTFE), said tubular member having a porosity;

at least one bead of fluoropolymer extending circumferentially about and forming transverse ridges disposed on and protruding above an exterior surface of said first tubular member at a regular pitch; and a PTFE membrane placed over said bead and coalesced to said first tubular member to provide a continuous undulant cover adhering over the ridges that modulates external profile of the assembled prosthesis to a reduced friction smooth surface profile while enhancing tissue ingrowth at said external profile and said membrane having a second porosity that is substantially less than the first tubular member to prevent needle punctures from causing premature physical failure of the membrane.

18. An improved tubular prosthesis for surgical implantation to replace a segment of a blood vessel, such prosthesis comprising a first member constituting a flow passage extending along a tube axis and formed of porous polymer, said first member having a porosity;

at least one support bead disposed on an exterior surface of said first member and extending circumferentially at a regular pitch to form spaced apart transverse ridges having a profile protruding above said exterior surface of said first member; and a tissue ingrowth membrane placed over said support bead and coalesced to said tube said tissue ingrowth membrane adhering over the ridges and bonding to said first member to enclose said ridges and provide kink and compression resistance without interlaminar peeling, said membrane further modulating said profile for atraumatic tunneling and also promoting fibroblast ingrowth thereby enhancing dialysis needle access of said prosthesis and said membrane having a second porosity that is substantially less than the first tubular member to prevent needle punctures from causing premature physical failure of the membrane.

* * * * *

UNITED STATES PATENT AND TRADEMARK OFFICE
CERTIFICATE OF CORRECTION

PATENT NO. : 5,897,587
DATED : April 27, 1999
INVENTOR(S) : Paul Martakos, Peter Gingras, Theodore Karwoski and Steve A. Herweck Page 1 of 1

It is certified that error appears in the above-identified patent and that said Letters Patent is hereby corrected as shown below:

<u>Column 5,</u>
Line 24, please replace "intemodal" with -- intermodal --.

Signed and Sealed this

Twenty-third Day of April, 2002

Attest:

JAMES E. ROGAN
*Attesting Officer*    *Director of the United States Patent and Trademark Office*